(12) United States Patent
Knorr et al.

(10) Patent No.: US 9,127,991 B2
(45) Date of Patent: Sep. 8, 2015

(54) CATHETER AND CATHETER ARRANGEMENT

(71) Applicant: VascoMed GmbH, Binzen (DE)

(72) Inventors: Stefan Knorr, Berlin (DE); Ingo Weiss, Berlin (DE); Stephan Fandrey, Affoltern am Albis (CH); Wolfgang Geistert, Rheinfelden (DE)

(73) Assignee: VascoMed GmbH, Binzen (DE)

( * ) Notice: Subject to any disclaimer, the term of this patent is extended or adjusted under 35 U.S.C. 154(b) by 149 days.

(21) Appl. No.: 13/742,000

(22) Filed: Jan. 15, 2013

(65) Prior Publication Data

US 2013/0190688 A1    Jul. 25, 2013

Related U.S. Application Data

(60) Provisional application No. 61/588,195, filed on Jan. 19, 2012.

(51) Int. Cl.
| | | |
|---|---|---|
| *A61M 31/00* | (2006.01) |
| *G01L 1/00* | (2006.01) |
| *A61B 5/00* | (2006.01) |
| *A61M 25/01* | (2006.01) |
| *A61B 19/00* | (2006.01) |
| *A61M 25/10* | (2013.01) |
| *A61N 1/05* | (2006.01) |
| *A61M 25/00* | (2006.01) |

(52) U.S. Cl.
CPC ................. *G01L 1/00* (2013.01); *A61B 5/6852* (2013.01); *A61B 5/6885* (2013.01); *A61B 19/46* (2013.01); *A61M 25/01* (2013.01); *A61M 25/10* (2013.01); *A61N 1/05* (2013.01); *A61B 2019/465* (2013.01); *A61M 2025/0002* (2013.01); *A61M 2025/0166* (2013.01)

(58) Field of Classification Search
CPC .......... A61B 2019/465; A61B 5/6885; A61M 2025/0002; A61M 25/10184; A61M 2025/1086; G01L 1/00
USPC .......................................... 604/98.01, 103.08
See application file for complete search history.

(56) References Cited

U.S. PATENT DOCUMENTS

| | | |
|---|---|---|
| 2008/0161796 A1 | 7/2008 | Cao et al. |
| 2008/0275428 A1 | 11/2008 | Tegg et al. |
| 2008/0294144 A1 | 11/2008 | Leo et al. |
| 2012/0265044 A1* | 10/2012 | Broens ........................ 600/373 |
| 2013/0150693 A1* | 6/2013 | D'Angelo et al. ............ 600/373 |

FOREIGN PATENT DOCUMENTS

DE          103 35 313          10/2005

OTHER PUBLICATIONS

European Search Report and Notes to the European Search Report on European Patent Application No. EP 12 19 2909, dated Jan. 25, 2013 (11 pages).

* cited by examiner

*Primary Examiner* — Kevin C Sirmons
*Assistant Examiner* — Deanna K Hall
(74) *Attorney, Agent, or Firm* — Buchanan Ingersoll & Rooney PC

(57) ABSTRACT

A catheter with an elongated catheter body which, with regard to a position of use, has a distal and a proximal end, wherein at the distal end, a sponge- or cushion-like elastic deformation body is arranged which has, in particular, electrically, mechanically or optically acting measuring means or a measuring connection for detecting a pressing force exerted on the deformation body.

16 Claims, 6 Drawing Sheets

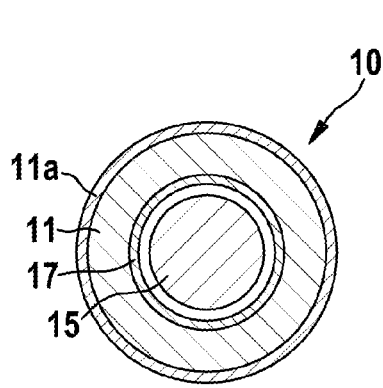
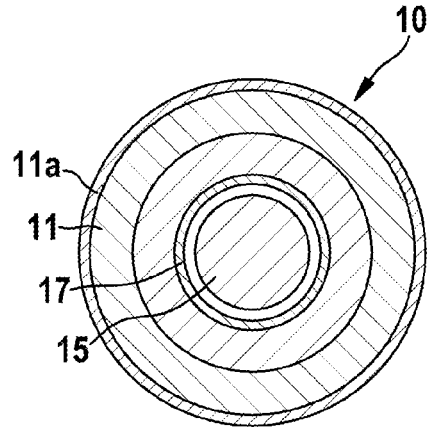
FIG. 1D          FIG. 1E
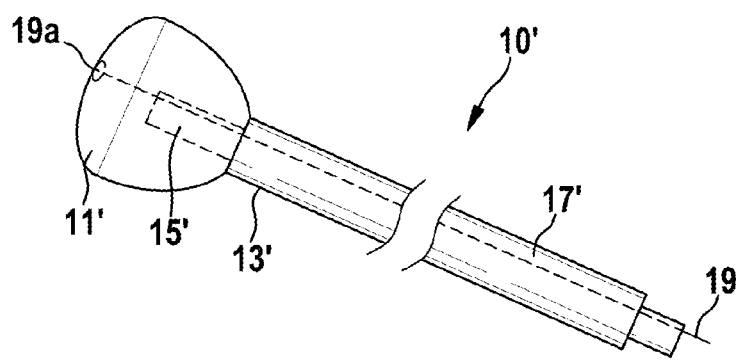
FIG. 2A
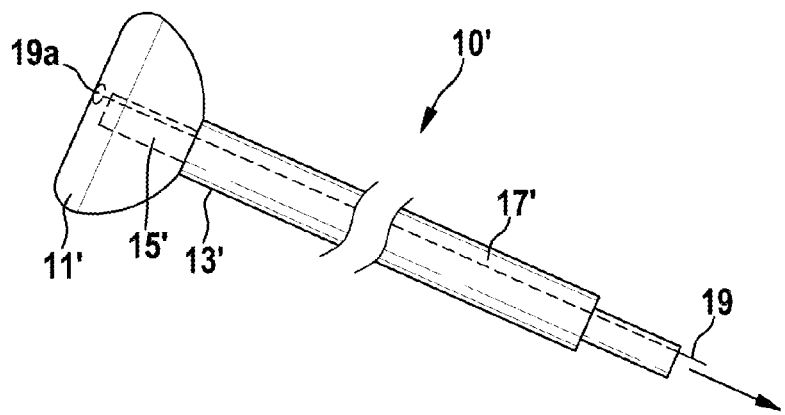
FIG. 2B

CATHETER AND CATHETER ARRANGEMENT

CROSS-REFERENCE TO RELATED APPLICATIONS

This patent application claims the benefit of U.S. Provisional Patent Application No. 61/588,195, filed on Jan. 19, 2012, which is hereby incorporated by reference in its entirety.

TECHNICAL FIELD

The present invention relates generally to a catheter with an elongated catheter body which, with regard to a position of use, has a distal and a proximal end. The present invention further relates to a catheter arrangement and a measuring device connected thereto.

BACKGROUND

In medical practice, a variety of differently designed catheter and/or catheter-like devices (e.g., electrode lines) are known and in widespread use. In some cases, they are used by experienced specialists; however, in some cases, they are used by physicians and/or also medical personnel without special knowledge and experience. Nevertheless, harm and/or impairment in the patient have to be reliably excluded.

When using known catheters having a plastic tip or a metal tip, there is a risk of perforation. In order to keep the surface pressure and, thus, the risk of perforation low, compromises in terms of stiffness of the catheter shaft and the catheter tip have to be accepted. These compromises limit, among other things, the maneuverability and the positional stability of the catheter.

The present invention is directed toward overcoming one or more of the above-identified problems.

SUMMARY

It is therefore an object of the present invention to provide an improved catheter which can also be used by less experienced persons, the construction of which nevertheless readily meets the requirements for clinical use, and the practical value of which is generally increased.

An object of the present invention is achieved by a catheter with the features of claim 1. The present invention further provides a catheter arrangement with the features of claim 16.

The present invention is based on the idea to modify known catheter structures by a special perforation protection element. The present invention further includes the idea to provide a deformation body at the distal end of the catheter. Finally, the present invention comprises the idea to obtain, via suitable measuring means, data from the deformation behavior of the deformation body which permit an improved evaluation of the specific situation of use. When the catheter is in use, the deformation body is subjected to a pressure change when pressed against the wall of a vessel or hollow organ, and the pressure change can be converted distally or proximally. The pressure change occurring when pressed against the tissue can result in a change of the electrical properties of the deformation body (e.g., resistance, capacitance, etc.), which can be measured and can be used for determining the pressure area and/or pressure force. A direct mechanical signal transmission is also possible.

In suitable configurations of the present invention, it is provided that the deformation body contains a plastic foam or a fluid, in particular a liquid or a gel, or a filling of pourable particles. Since the deformation body has to react elastically, a filling level adapted to the surface and nature of the sheath layer is to be considered when filling in a fluid.

In a metrological embodiment already generally mentioned above, measuring electrodes, each with one measuring voltage connection, are provided in shell sections of the deformation body which oppose each other. In one configuration, the deformation body comprises a foam from an electrically conductive polymer or with electrically conductive, finely distributed inclusions, or with conductive particles which are coated with a dielectric, or has particles from a ferroelectric film.

In further configurations of the present invention it is provided that at the distal end, and rigidly connected thereto, a first measuring device element is provided, and a second measuring device element interacting with the first measuring device element is provided on the inner wall of a sheath of the deformation body. Due to its own elasticity, and/or its interaction with a filling, and/or its interaction with at least one spring element which supports the sheath with respect to the catheter body, the sheath of the deformation body is configured in a self-resetting manner.

A particularly simple, purely mechanical embodiment of the provided measuring means can be configured such that at a distal end of the deformation body, a freely displaceable measuring wire is provided which extends up to the proximal end of the catheter and runs within the catheter body. The stiff measuring wire's displacement along the catheter body, caused by the compression of the deformation body, is visible and quantitatively detectable at the proximal end of the catheter body; however, a force measurement requires additional metrological provisions. In one modification, the function of the measuring wire can also be assumed up to a certain extent by the inner hose itself.

In a further embodiment, the deformation body is a multi-piece design from a plurality of sub-bodies, wherein the sub-bodies have a different deformation behavior and/or separate measuring means or connections for detecting a pressing force specifically exerted on said sub-bodies. It is in particular provided in this embodiment that the sub-bodies comprise optically or electrically acting measuring means or connections.

In a further embodiment, the inventive catheter is configured as an electrode line with at least one electrode arranged on the deformation body or at the distal end of the inner hose enclosed by the deformation body. Here, in particular, the, or at least one, electrode is elastically deformable and is in particular, for example, made from a conductive plastic.

Further features, aspects, objects, advantages, and possible applications of the present invention will become apparent from a study of the exemplary embodiments and examples described below, in combination with the figures, and the appended claims

DESCRIPTION OF THE DRAWINGS

Advantages and usefulness of the present invention arise also from the following schematic description of exemplary embodiments based on the figures. In the figures:

FIGS. 1A-1E show schematic illustrations (side views and cross-sectional illustrations) of an embodiment of the catheter according to the present invention in the initial state and in the deformed state of the catheter end;

FIGS. 2A-2B show schematic perspective illustrations of a further embodiment of the inventive catheter;

DETAILED DESCRIPTION

Figure 1A:
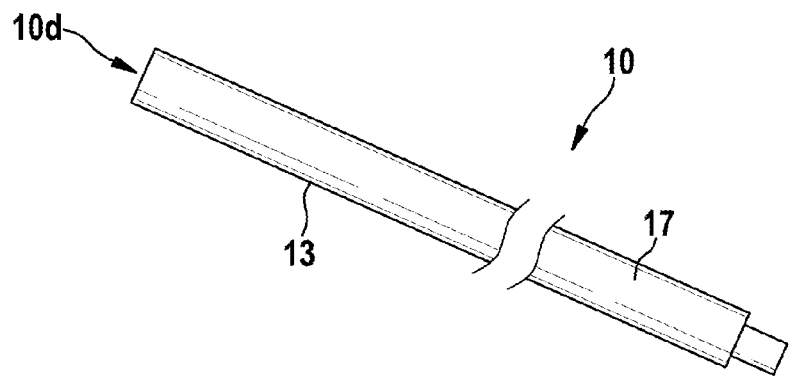
Figure 1B:
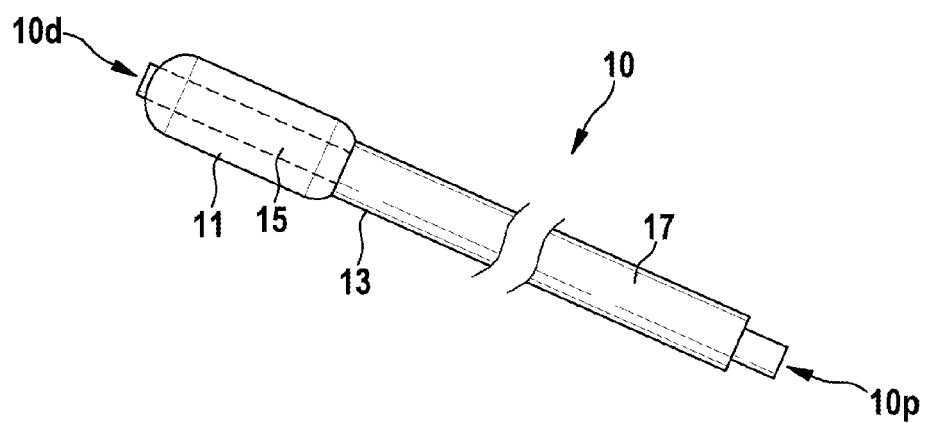
Figure 1C:
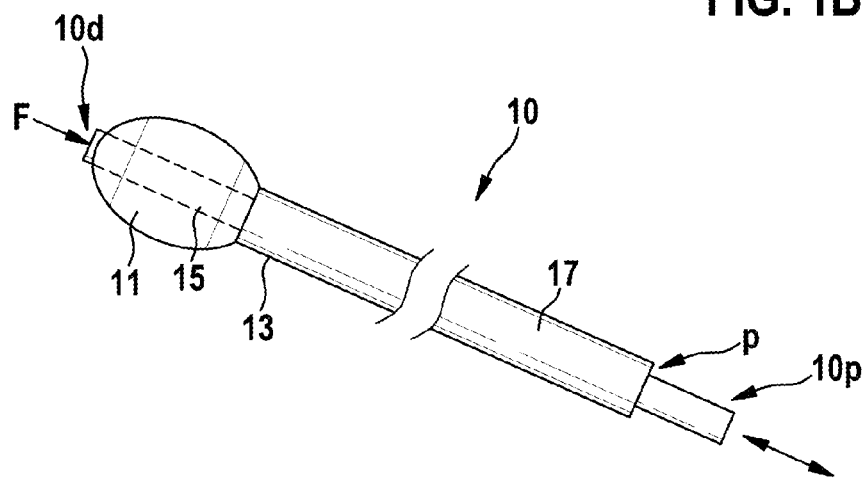

FIGS. 1A-1E show schematically a catheter 10 with a distal end 10d and a proximal end 10p, wherein a deformation body 11 is attached at the distal end 10d. The illustrated embodiment involves a foamed plastic body with a dimensionally elastic sheath 11a which, upon contact of the distal catheter end 10d with the wall, as shown in FIG. 1C, deforms into a curved shape.

A catheter body 13 of the catheter 10 comprises an inner hose 15 and an outer hose 17 which can be proximally displaced relative to the inner hose 15. The deformation body 11 is secured at the distal end of the inner hose 15, and the outer hose 17, in an initial state of the catheter 10 (see FIG. 1A), fully covers the inner hose 15 as well as the deformation body 11, which encloses the inner hose 14 in the distal region, and allows the deformation body 11 to unfold only after it is pulled back far enough. (See FIG. 1B). Due to the displaceability of the inner 15 and outer 17 hoses relative to one another, as shown in FIG. 1C, the action of a pressure force "F" onto the distal end 10d of the catheter 10 results not only in a deformation of the balloon 11, but also in a displacement of the inner hose 15 relative to the outer hose 17 in the proximal direction. This displacement can be detected and evaluated; with respect to the metrological use of the proposed catheter, see also the explanations below.

FIGS. 2A-2B show a further catheter according to the present invention, wherein the selected reference numbers are based on FIGS. 1A-1E, and explanations given above with regard to the first embodiment are not repeated here.

FIG. 2A shows an initial state and FIG. 2B shows a state of use under the influence of a distally acting force "F". The catheter 10' differs from the one shown in the FIGS. 1A-1E and described above in that the deformation body 11' protrudes beyond the distal end of the inner hose 15'. A wall contact with the wall of a vessel or hollow organ in the distal direction thus results first in a compression of the deformation body 11', as shown in FIG. 2B. Only a further forward displacement results finally (besides a further development of said compression or deformation) in a sufficiently high pressure on the distal end of the inner hose 15 so that the latter moves in the proximal direction. However, the catheter 10' can also be structured such that—after releasing the deformation body 11' by pulling back the outer hose 17'—the inner hose 15' is locked with respect to the outer hose 17' and cannot deflect in the proximal direction.

As in the first-mentioned embodiment, due to the displacement in connection with the deformation of the deformation body 11', the surface pressure at the distal catheter end and, thus, the risk of perforation, is reduced. Providing a deformation measuring wire 19, which extends through the entire length of the inner hose 15' of the catheter 10' and which is fixed via a fixing pad 19a at the point located most distal on the deformation body 11', allows, in addition, an approximate detection of the deformation of the deformation body 11' taking place upon a wall contact. In particular, the deformation body 11' is displaced to the extent of the occurring deformation in the proximal direction, as symbolically illustrated in FIG. 2B by the arrow at the proximal end.

Figure 3C:
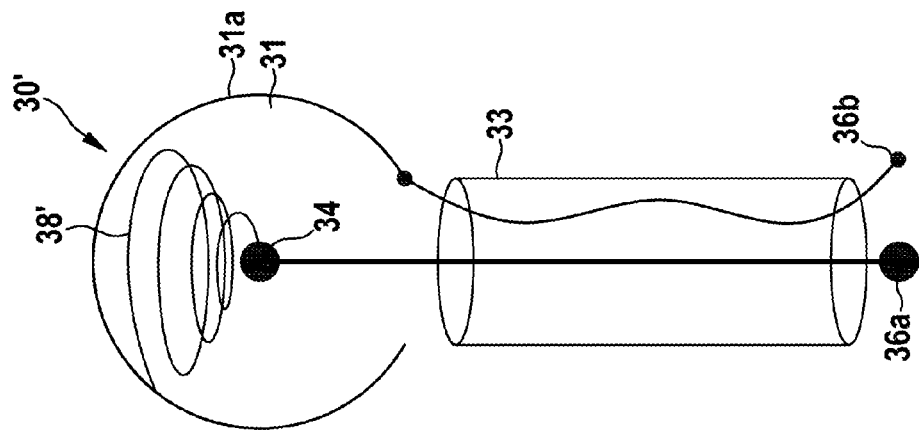
FIGS. 3A-3C show schematic perspective illustrations of a further embodiment of the inventive catheter.
Figure 3B:
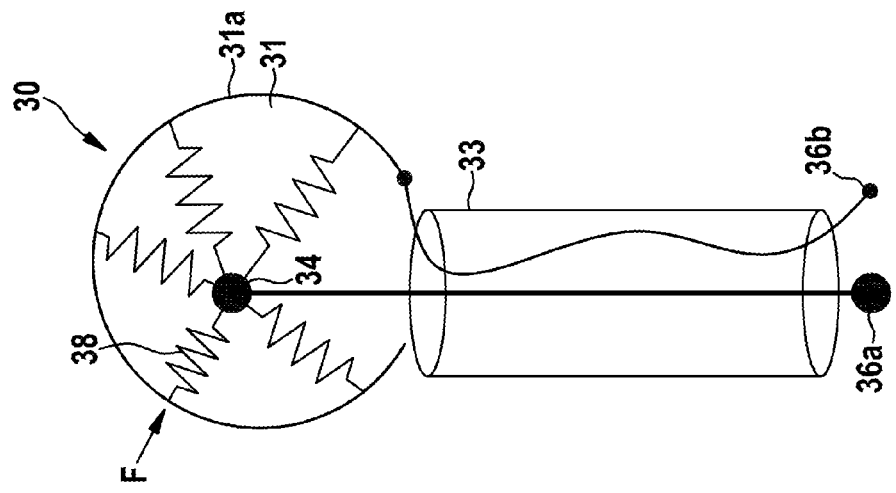
Figure 3A:
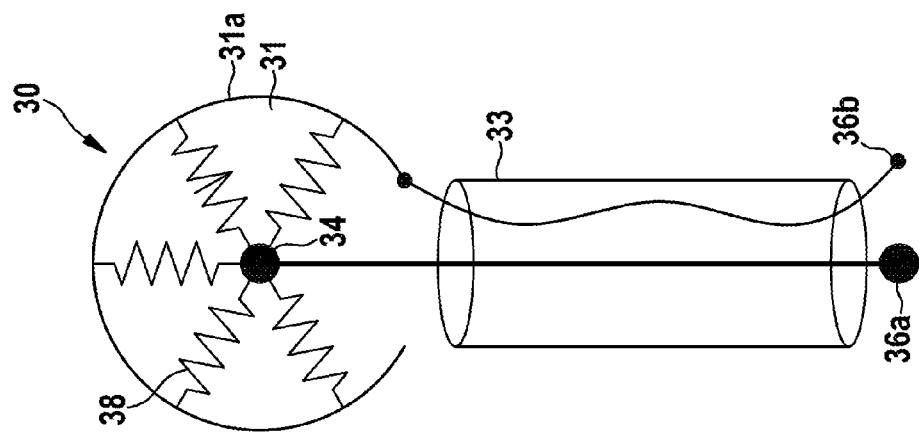

FIGS. 3A-3B show schematically the functional principle of a further embodiment of the proposed catheter, namely, a catheter 30 with a deformation body 31 at the distal end of a catheter body 33 which (in the context of the function described below) is regarded as being rigid. In its center axis, the catheter 30 comprises a first pole 34 of an electrical (for example, inductive) measuring device, the second pole of which is formed by the (particularly conductive) sheath 31a of the deformation body 31. Both measuring poles 34, 31a are, in each case, connected to a proximal measuring connection 36a, 36b of the catheter 30. The (conductive) sheath or shell layer 31a is elastically braced in a self-centering manner with respect to the centrally fixed first measuring pole 34 by a plurality of spring elements 38. For clarification of the functional principle, the spring elements 38 are drawn as springs; however, in practice, this can involve deformation elements with a different structure, wherein in the context of the above-mentioned inductive measurement, a function as inductivities can be useful, as will be appreciated by one of ordinary skill in the art.

As shown in FIG. 3B, the configuration of spring elements 38 and sheath 31a of the deformation body 31 is displaced under the influence of a force "F" which results in the generation of an electrical measuring signal at the connections 36a, 36b. This signal correlates with the amount of displacement and/or deformation of the deformation body 31, and is therefore useful as a measure for the force acting on the wall. The dependence of the measuring signal on the deformation is retrieved, e.g., from a predetermined look up table. Depending on the actual configuration, an arrangement of the type shown can function as an inductive or capacitive or even as an ohmic measuring sensor or, where applicable, can realize a combination of a plurality of measuring principles.

FIG. 3C shows a modified catheter 30', the structure of which corresponds substantially to the one of the catheter 30 according to FIGS. 3A-3B, wherein, however, the arrangement of a plurality of spring elements 38 (see FIGS. 3A-3B) is replaced by a single, special spirally shaped spring element 38'. With regard to the implementable measuring principles, the above statements apply principally also to this modification.

Figure 4:
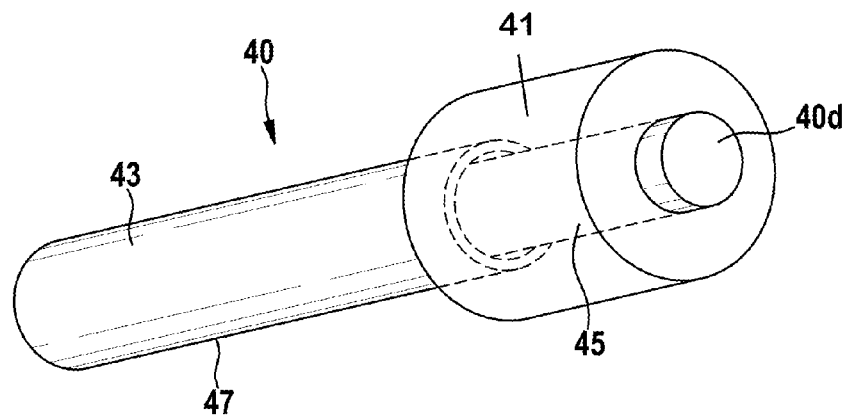
FIG. 4 shows a perspective illustration of a further embodiment of the catheter according to the present invention.

As another embodiment of the present invention, FIG. 4 schematically shows a three-section catheter 40, wherein the catheter body 43 (including inner hose 45 and outer hose 47), as well as the deformation body 41, is divided into three cylinder segments. If during use, the catheter 40 has wall contact near its distal end 40d with the wall of a vessel or hollow organ, this wall contact has a different effect on the individual sections of the deformation body 41 and, for example, through the detection of the electrical resistance of the individual parts, not only the total force but also the direction can be determined, and thus additional knowledge about the position of the catheter 40 can be obtained.

Figure 5:
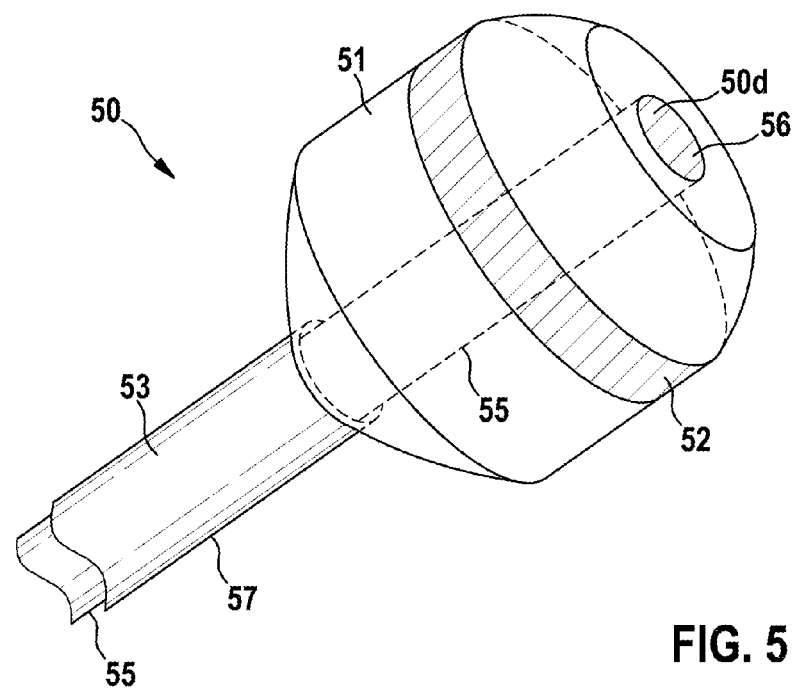
FIG. 5 shows a schematic illustration of an embodiment of the proposed inventive catheter as a bipolar electrode line.

FIG. 5 schematically shows the distal end of an electrode catheter 50 according to the present invention with a deformation body 51 and a catheter body 53 which comprises an inner hose 55 and an outer hose 57 and, in its distal region, carries two electrodes which can be used for tissue stimulation and/or for sensing tissue potentials. At the distal end 50d of the electrode catheter 50, a tip electrode 56 is provided which can be generated, for example, through a metal coating of the distal end of the inner hose 55. Also, provided on the circumference of the deformation body 51 is a ring electrode 52 which can be formed, for example, from an elastic conductive plastic. As an alternative, providing a meandering-shaped metal strip or the like is also possible.

Figure 6:
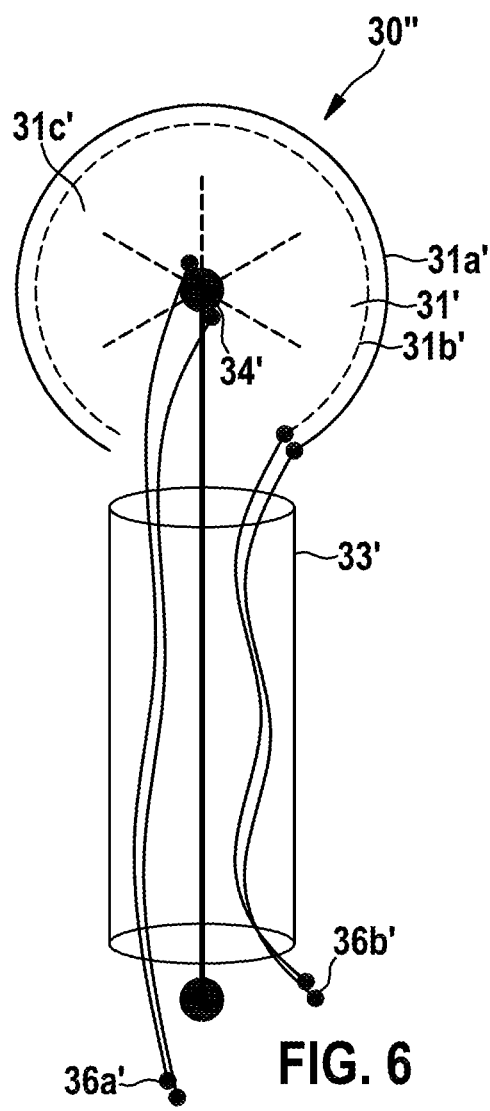
FIG. 6 shows a schematic illustration of a further embodiment of the catheter according to the present invention.

FIG. 6 schematically shows a further catheter, wherein the designation of the parts is based on the ones of the catheter 30 according to FIGS. 3A-3B. The catheter is generally designated by the number 30" and comprises a deformation body 31' and a catheter body 33' which is to be regarded as being rigid, wherein a first measuring device element 34' is provided positioned on the axis of the catheter 30" and is stationary with respect to the catheter body 33', and a second measuring device element 31b' is provided on the inner side of the sheath of the deformation body 31'.

Deviating from the embodiment according to FIGS. 3A-3B, the measuring device of FIG. 6 involves an optical measuring device, and the first measuring device element 34' is a light source uniformly emitting all around, and the second measuring device element 31b' is a spherical array of solar cells. The deformation body 31' is filled with a fluid having a light-damping effect such as, for example, a cloudy elastogel 31c'. The light source 34' is connected through first proximal connections 36a' to an external power supply (not illustrated), and the solar cell array 31b' is connected via second proximal connections 36b' to an external measuring and evaluating unit (not illustrated).

The light source 34' radiates through the light-damping medium 31c' and the arriving radiation is continuously integrated by the spherical array of solar cells 31b'. The spherical array of solar cells 31b' on the inner surface of the sheath 31' can be generated, for example, by means of a printing method which has recently been considered for generating solar cells. The integral value changes when the light portions, due to their displacement out of the center of the deformation body 31' (caused by forces acting on the deformation body 31'), have to cover longer distances through the light-damping medium 31c' and, thus, are damped in a manner different from the undisturbed resting state of the deformation body 31'.

Figure 7A:
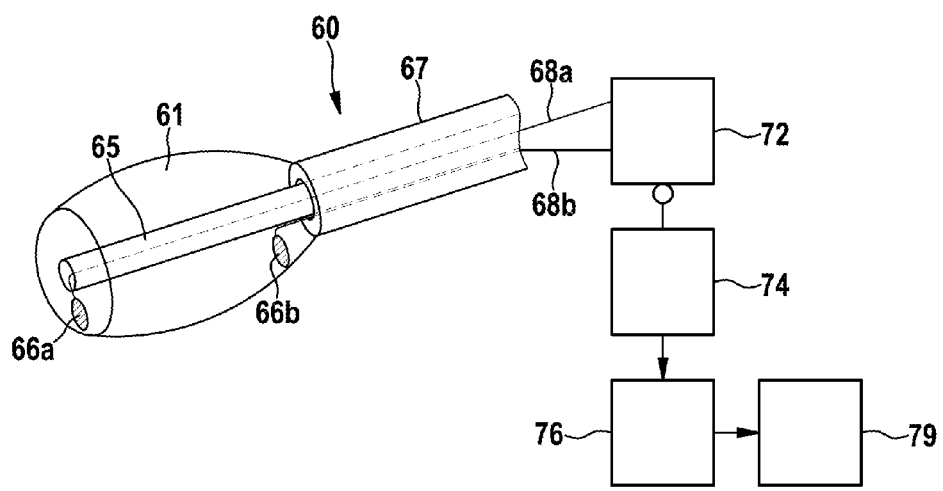
FIGS. 7A-7B show schematic diagrams of embodiments of the catheter arrangement according to the present invention.

FIG. 7A shows a catheter arrangement with a catheter 60 which has a plastic foam body 61 made from a conductive foam and serving as a deformation body.

Detecting the deformation of the deformation body 61, which has a conductive foam which, based on direction-dependent changes in impedance, responds to deformation degree and direction, takes place via two measuring electrode surfaces 66a, 66b in the distal and proximal region, respectively, of the deformation body 61. Said measuring electrode surfaces 66a, 66b are connected via measuring lines 68a and 68b to a measuring current supply 72 with an associated current sensor 74. An evaluating unit 76 and finally a display unit 79 for providing wall contact information for the surgeon or other medical personnel are connected downstream of the current sensor 74. A deformation of the deformation body 61 results in a decrease of the distance between the measuring electrodes 66a, 66b and, at the same time, results in a compression of the foam which is expressed in a change of the resistance in the current path between the measuring electrodes 66a, 66b and thus in a change of the amperage. The evaluation of the amperage provides the necessary information about the existence of a wall contact and its intensity.

Figure 7B:
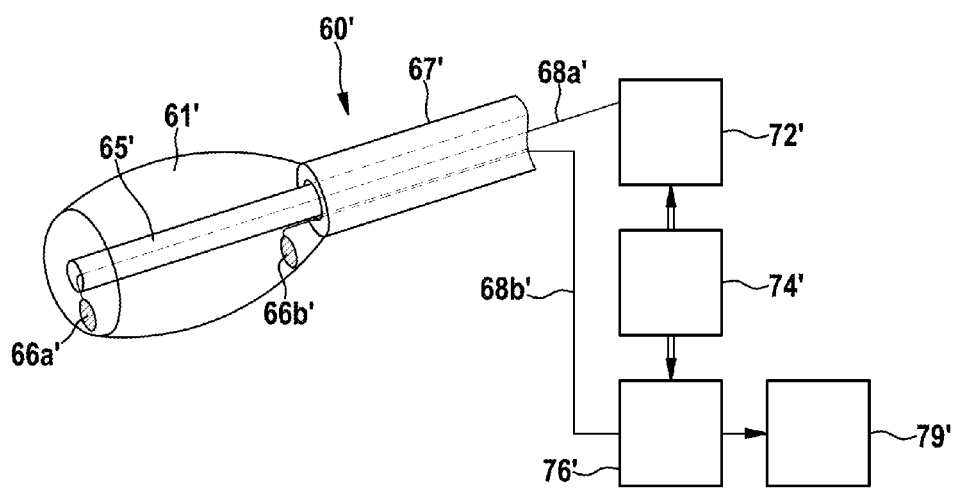

Similarly structured is the embodiment with a catheter 60', schematically shown in FIG. 7B, the deformation body 61' of which has a plastic foam composition which is transparent to a certain degree. Said deformation body 61' allows the detection of the weakening of the light passing in the longitudinal direction through the deformation body 61' during a compression of the latter (e.g., as sketched in FIG. 2B). Accordingly, instead of measuring electrodes, an optical transmitter element (e.g., an LED) 66a' and an optical receiver element (e.g., a photodiode) 66b' are provided which are connected via electrical supply lines 66a' and 66b' to an adequately adapted measuring current supply 72' and an evaluating unit 76', respectively, which are controlled via an operating control unit 74'. The arrangement comprises again a display unit 79' on which the measurement results are visualized for the surgeon or other medical personnel.

The embodiments of the present invention are not limited to the above-described examples and emphasized aspects but, rather, are also possible in a multiplicity of modifications, all of which lie within the scope of persons skilled in the art.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A catheter comprising:
an elongated catheter body which, with regard to a position of use, has a distal and a proximal end, wherein at the distal end, a sponge- or cushion-like elastic deformation body is arranged which is configured to deform as the catheter body is inserted into a patient and which comprises electrically, mechanically or optically acting measuring means or a measuring connection for detecting a pressing force exerted on said deformation body.

2. The catheter according to claim 1, wherein the deformation body contains a plastic foam or a fluid, the fluid comprising a liquid or a gel, or a filling of pourable particles.

3. The catheter according to claim 1, wherein, in shell sections of the deformation body which oppose each other, measuring electrodes, each with one measuring voltage connection, are provided.

4. The catheter according to claim 1, wherein, in shell sections of the deformation body which oppose each other, an optical transmitting and receiving element with a power supply and measuring connection, respectively, is provided.

5. The catheter according to claim 1, wherein the deformation body has a dimensionally elastic sheath or shell layer.

6. The catheter according to claim 1, wherein the catheter comprises an electrode line with at least one stimulation and/or sensing electrode arranged on the deformation body.

7. The catheter according to claim 6, wherein the at least one stimulation and/or sensing electrode is formed elastically deformable and made of a conductive plastic.

8. The catheter according to claim 1, wherein in a relaxed, non-deformed state, the deformation body has a spherical, or ellipsoidal or cylindrical shape.

9. The catheter according to claim 1, further comprising a plurality of measuring means or measuring connections which are independent of each other.

10. A catheter arrangement comprising:
a catheter according to claim 1; and
a measuring device connected to the, or each, measuring means or connection for determining a pressing force acting on the deformation body or sections thereof.

11. A catheter comprising:
an elongated catheter body which, with regard to a position of use, has a distal and a proximal end, wherein at the distal end, a sponge- or cushion-like elastic deformation body is arranged which comprises electrically, mechanically or optically acting measuring means or a measuring connection for detecting a pressing force exerted on said deformation body, wherein, in shell sections of the deformation body which oppose each other, measuring electrodes, each with one measuring voltage connection, are provided, and wherein the deformation body includes a foam made from an electrically conductive polymer or with electrically conductive, finely distributed inclusions or with conductive particles which are coated with a dielectric, or has particles made from a ferroelectric film.

12. A catheter comprising:

an elongated catheter body which, with regard to a position of use, has a distal and a proximal end, wherein at the distal end, a sponge- or cushion-like elastic deformation body is arranged which comprises electrically, mechanically or optically acting measuring means or a measuring connection for detecting a pressing force exerted on said deformation body, wherein, in shell sections of the deformation body which oppose each other, an optical transmitting and receiving element with a power supply and measuring connection, respectively, is provided, and wherein the deformation body has finely distributed light-reflecting inclusions and/or a sheath or shell layer reflecting light on the inside.

13. A catheter comprising:

an elongated catheter body which, with regard to a position of use, has a distal and a proximal end, wherein at the distal end, a sponge- or cushion-like elastic deformation body is arranged which comprises electrically, mechanically or optically acting measuring means or a measuring connection for detecting a pressing force exerted on said deformation body, wherein at the distal end of the catheter body, rigidly connected therewith, a first measuring device element is provided and, on an inner wall of a sheath of the deformation body, a second measuring device element interacting with the first measuring device element is provided, and the sheath of the deformation body, due to its own elasticity and/or its interaction with a filling, and/or its interaction with at least one spring element supporting the sheath with respect to the catheter body, is configured to be self-resetting with respect to the catheter body.

14. A catheter comprising:

an elongated catheter body which, with regard to a position of use, has a distal and a proximal end, wherein at the distal end, a sponge- or cushion-like elastic deformation body is arranged which comprises electrically, mechanically or optically acting measuring means or a measuring connection for detecting a pressing force exerted on said deformation body, wherein at a distal end of the deformation body, a measuring wire is attached which extends up to the proximal end of the catheter and runs freely displaceable in the catheter body.

15. A catheter comprising:

an elongated catheter body which, with regard to a position of use, has a distal and a proximal end, wherein at the distal end, a sponge- or cushion-like elastic deformation body is arranged which comprises electrically, mechanically or optically acting measuring means or a measuring connection for detecting a pressing force exerted on said deformation body, wherein the deformation body is a multi-piece design formed from a plurality of sub-bodies, wherein the sub-bodies have a different deformation behavior and/or separate measuring means or connections for detecting a pressing force specifically exerted on said sub-bodies.

16. The catheter according to claim 15, wherein the sub-bodies have optically and/or electrically acting measuring means or connections.

* * * * *